United States Patent [19]

Cox et al.

[11] Patent Number: 5,146,510
[45] Date of Patent: Sep. 8, 1992

[54] METHODS AND APPARATUS FOR OPTICALLY DETERMINING THE ACCEPTABILITY OF PRODUCTS

[75] Inventors: Kenneth A. Cox; Henry M. Dante; Robert J. Maher, all of Midlothian, Va.

[73] Assignee: Philip Morris Incorporated, New York, N.Y.

[21] Appl. No.: 661,809

[22] Filed: Feb. 27, 1991

Related U.S. Application Data

[63] Continuation-in-part of Ser. No. 308,739, Feb. 9, 1989, Pat. No. 5,046,111.

[51] Int. Cl.[5] .............................................. G06K 9/00
[52] U.S. Cl. .................................................. 382/8; 382/1; 358/101; 358/106; 358/107
[58] Field of Search ............... 382/8, 30, 34; 358/101, 358/106, 107; 356/71

[56] References Cited

U.S. PATENT DOCUMENTS

| | | | |
|---|---|---|---|
| 3,835,332 | 9/1974 | Bridges | 250/563 |
| 4,021,778 | 5/1977 | Veda et al. | 382/30 |
| 4,030,068 | 6/1977 | Banz | 382/30 |
| 4,053,056 | 10/1977 | Day | 209/73 |
| 4,097,845 | 6/1978 | Bacus | 340/146.3 |
| 4,110,737 | 8/1978 | Fahey | 382/30 |
| 4,119,946 | 10/1978 | Taylor | 382/34 |
| 4,481,664 | 11/1984 | Linger et al. | 382/8 |
| 4,482,971 | 11/1984 | Blazek | 364/552 |
| 4,637,054 | 1/1987 | Hashim | 382/8 |
| 4,759,074 | 7/1988 | Iadipaola et al. | 382/23 |
| 4,872,024 | 10/1989 | Nagai et al. | 346/1.1 |
| 4,912,554 | 3/1990 | Neri | 358/106 |
| 4,926,491 | 5/1990 | Maeda et al. | 382/14 |
| 4,952,062 | 8/1990 | Bean, III et al. | 356/430 |
| 4,972,262 | 11/1990 | Nichols | 358/160 |
| 4,972,494 | 11/1990 | White et al. | 382/8 |
| 4,974,261 | 11/1990 | Nakahara et al. | 382/22 |
| 4,975,971 | 12/1990 | Ohnishi | 382/8 |
| 4,975,972 | 12/1990 | Bose et al. | 382/8 |
| 5,014,327 | 5/1991 | Potter et al. | 382/30 |

FOREIGN PATENT DOCUMENTS

| | | |
|---|---|---|
| 0155789 | 1/1985 | European Pat. Off. . |
| 0330495 | 2/1989 | European Pat. Off. . |
| 63-257083 | 10/1988 | Japan . |
| WO89/10596 | 5/1989 | World Int. Prop. O. . |

OTHER PUBLICATIONS

R. C. Gonzalez, *Digital Image Processing*, Addison-Wesley Publishing Company 1987, pp. 331-341.
W. K. Pratt, *Digital Image Processing*, John Wiley & Sons, Inc., 1978, pp. 478-492.

*Primary Examiner*—Jose Couso
*Attorney, Agent, or Firm*—Robert R. Jackson

[57] ABSTRACT

The acceptability of the appearance of objects such as consumer products is determined by forming an initial discriminant function as a composite of a relatively small number of images which are known to be acceptable. This initial discriminant function is then used to gather statistical information about how a first relatively large number of images compares to the initial discriminant function. Thereafter, this statistical information is used to select or aid in the selection of acceptable images from a second relatively large number of images, and the images selected as acceptable are used to refine the discriminant function. The refined discriminant function is then used (e.g., during actual product inspection) to determine which objects have an acceptable appearance and which do not.

44 Claims, 14 Drawing Sheets

FROM FIG. 2a

300

TRAINING PHASE 3: USE THE FIRST AND SECOND THRESHOLD VALUES TO DETERMINE WHICH OF A RELATIVELY LARGE NUMBER OF "THIRD PHASE" IMAGES TO USE IN PROGRESSIVELY REFINING THE DISCRIMINANT FUNCTION FOR FURTHER USE. IF THE PROCESSED VALUE RESULTING FROM USE OF THE CURRENT DISCRIMINANT FUNCTION ON A GIVEN THIRD PHASE IMAGE IS BETWEEN THE FIRST THRESHOLD VALUES, USE THAT IMAGE TO REFINE THE DISCRIMINANT FUNCTION BEFORE PROCESSING THE NEXT THIRD PHASE IMAGE. IF THE PROCESSED VALUE IS NOT BETWEEN THE SECOND THRESHOLD VALUES, DISCARD THAT IMAGE. IF THE PROCESSED VALUE IS NOT BETWEEN THE FIRST THRESHOLD VALUES, BUT IS BETWEEN THE SECOND THRESHOLD VALUES, ALLOW THE OPERATOR OF THE SYSTEM TO DECIDE WHETHER THE IMAGE IS ACCEPTABLE. IF SO, USE THE IMAGE TO REFINE THE DISCRIMINANT FUNCTION BEFORE PROCESSING THE NEXT IMAGE. OTHERWISE DISCARD THE IMAGE.

400

ACTUAL PRODUCT INSPECTION: USE THE REFINED DISCRIMINANT FUNCTION TO COMPUTE A PROCESSED VALUE FOR THE IMAGE OF EACH PRODUCT. IF THE PROCESSED VALUE IS BETWEEN THE FIRST THRESHOLD VALUES, ACCEPT THE PRODUCT. OTHERWISE REJECT THE PRODUCT.

*FIG. 2b*

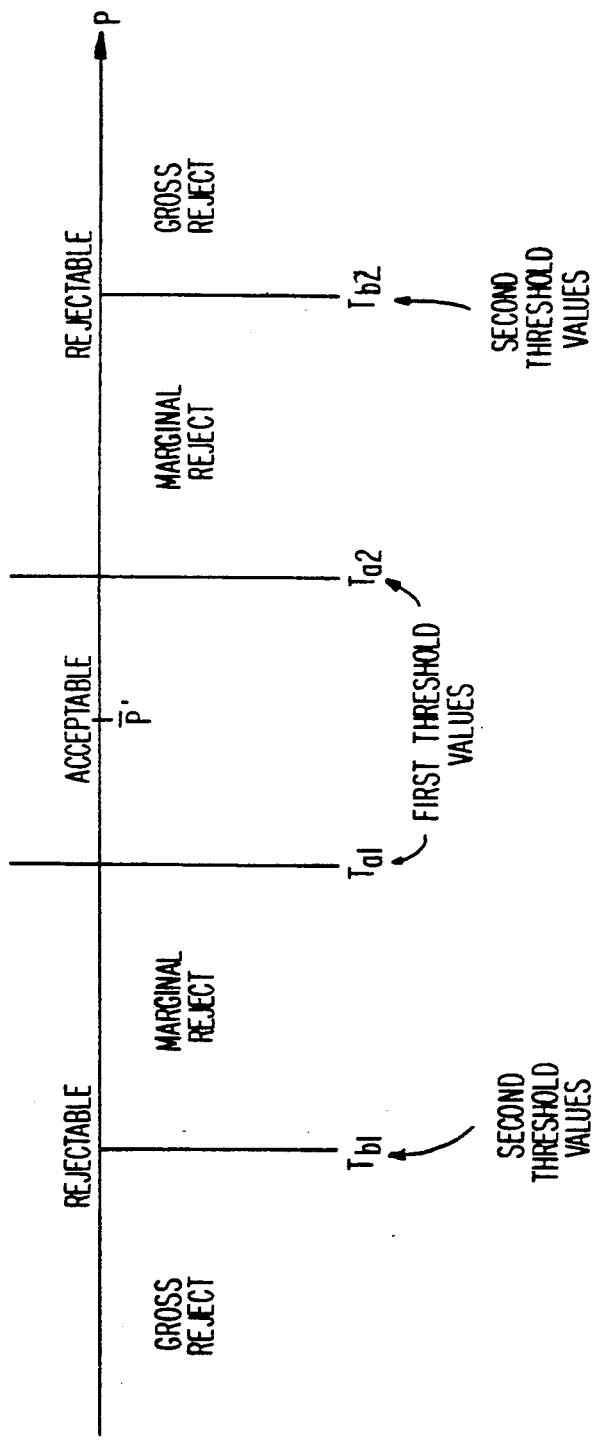

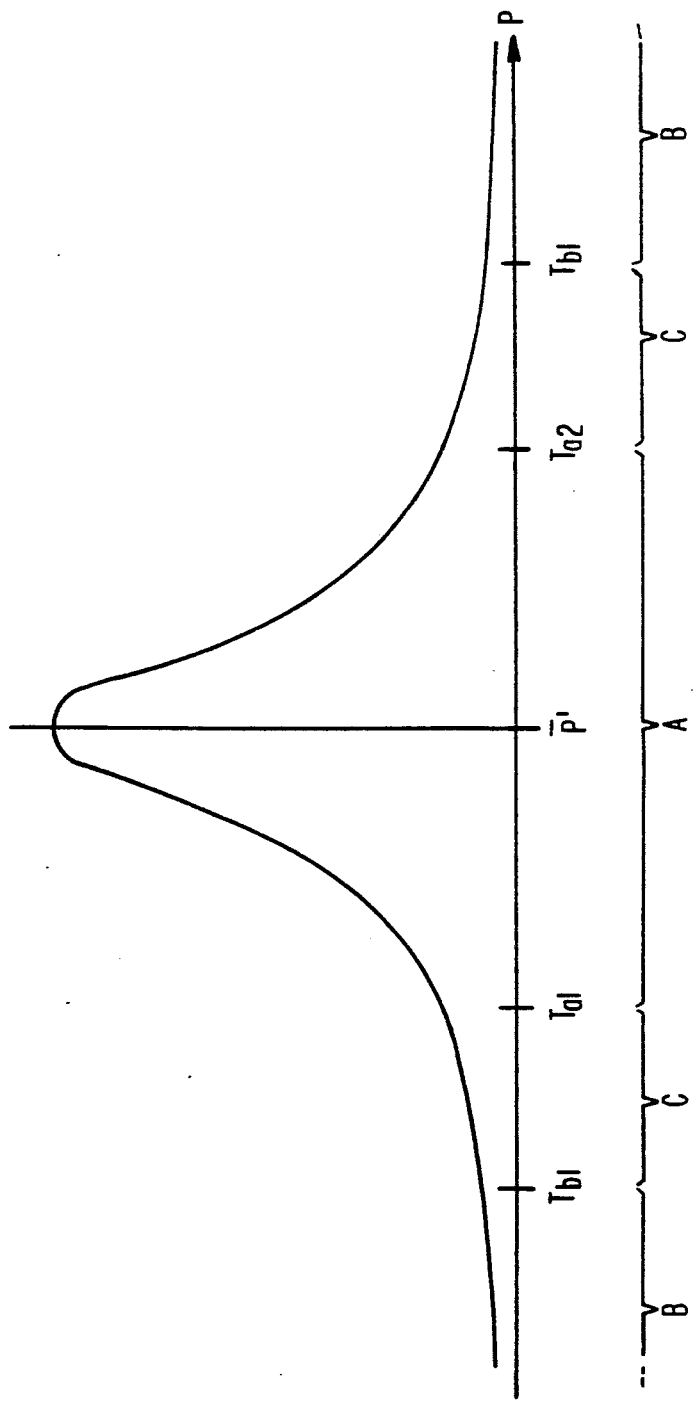

METHODS AND APPARATUS FOR OPTICALLY DETERMINING THE ACCEPTABILITY OF PRODUCTS

This is a continuation-in-part of application Ser. No. 308,739 filed Feb. 9, 1989 and issued Sep. 3, 1991 as U.S. Pat. No. 5,046,111.

BACKGROUND OF THE INVENTION

This invention relates to product inspection methods and apparatus, and more particularly to methods and apparatus for optically determining whether or not a product has an acceptable appearance.

For many products such as consumer goods like packaged foods, beverages, cleaning products, health and beauty aids, cigarettes, cigars, etc., it is very important that the external appearance of the product or its packaging be uniform and defect-free. Yet these products are typically produced in such large quantities and at such high speeds that some form of automated optical inspection is practically essential. It is highly desirable for an optical inspection system to be able to test all or substantially all parts of the product image so that defects of any kind occurring anywhere in the image can be detected. At the same time the inspection system should not reject products having minor but acceptable deviations from the ideal product.

For even a relatively simple product image such as a cigarette pack, an inspection system must be initially supplied with a tremendous amount of information in order to enable the system to inspect all or substantially all portions of the image with the sophistication required to discriminate between acceptable products (i.e., products having the ideal appearance or an appearance acceptably close to the ideal) and unacceptable products which should be rejected because of defects in appearance or appearance which is not sufficiently close to the ideal. Identifying and entering this information into the inspection system apparatus typically requires a very high level of skill and/or large amounts of operator time. Moreover, this data identification and entry task must be repeated each time a new or even slightly different product is to be inspected.

It is therefore an object of this invention to improve and simplify optical inspection systems.

It is a more particular object of this invention to provide optical inspection systems which greatly reduce the level of operator skill and amount of operator time required to set up the system to inspect a new or different product.

SUMMARY OF THE INVENTION

These and other objects of the invention are accomplished in accordance with the principles of the invention by providing optical inspection systems which form an initial discriminant function or "filter" from a composite of a relatively small number of "first phase" images which the operator of the system determines to be acceptable images. A relatively simple technique (e.g., a logical OR function) is preferably used to form this composite. The ability to produce the initial discriminant function quickly using such a simple combination of a small number of images facilitates rapid "start-up" of the system. Thereafter the system uses the initial discriminant function to process a relatively large number of representative "second phase" images in order to compute statistical information about the images in relation to the initial discriminant function. In particular, the system uses the initial discriminant function to compute a processed value for each second phase image. These processed values will typically have an approximately normal or Gaussian distribution. The upper and lower limits of a central portion of this distribution containing a first statistically large number of the processed values are identified as first threshold values. The upper and lower limits of a central portion of this distribution containing a second statistically even larger number of the processed values are identified as second threshold values.

In a subsequent third phase of the operation of the system, the first and second threshold values are used in the processing of a relatively large number of "third phase" images. In particular, the system uses a discriminant function (initially the above-mentioned initial discriminant function) to compute a processed value for each successive third phase image. If this processed value for a given third phase image is between the first threshold values, that third phase image is automatically used to refine (e.g., using a Widrow-Hoff-type adaptive training process) the discriminant function for subsequent use. If the processed value for a third phase image is not between the second threshold values, that third phase image is automatically discarded. As a third possibility, if the processed value for a third phase image is not between the first threshold values but is between the second threshold values, the operator of the system is given the choice as to whether or not that image should be discarded (i.e., because the image looks unacceptable) or used to refine the discriminant function for subsequent use (i.e., because the image looks acceptable).

When the third phase is completed, the system is ready for actual product inspection using the refined discriminant function and the first threshold values. In actual product inspection, the system uses the refined discriminant function to compute a processed value for each product image. If the processed value for a product image is between the first threshold values, the product is accepted as having an acceptable appearance. If the processed value for a product image is not between the first threshold values, the product is rejected as having an unacceptable appearance.

The system greatly reduces the level of operator skill and amount of operator time required to set the system up for a product inspection task. The operator is only required to identify a relatively small number of acceptable images (e.g., 25) during the first phase. The initial discriminant function is then computed automatically using a simple and rapid technique such as a logical OR of the small number of first phase images. The entire second phase may also be automatic. And during the third phase, the operator is only required to decide on the acceptability of the relatively small number of images whose processed values fall outside the first threshold values but between the second threshold values.

Further features of the invention, its nature and various advantages will be more apparent from the accompanying drawings and the following detailed description of the preferred embodiments.

BRIEF DESCRIPTION OF THE DRAWINGS

FIGS. 2a and 2b (referred to collectively as FIG. 2) are a flow chart of an illustrative optical product inspection method in accordance with this invention.

FIG. 7 is a diagram of a dot product spectrum which is useful in explaining certain features of the invention.

FIG. 8 is a histogram diagram useful in explaining certain features of the invention.

FIG. 9 shows several equations which may be employed in accordance with the invention.

DETAILED DESCRIPTION OF THE PREFERRED EMBODIMENTS

Figure 1:
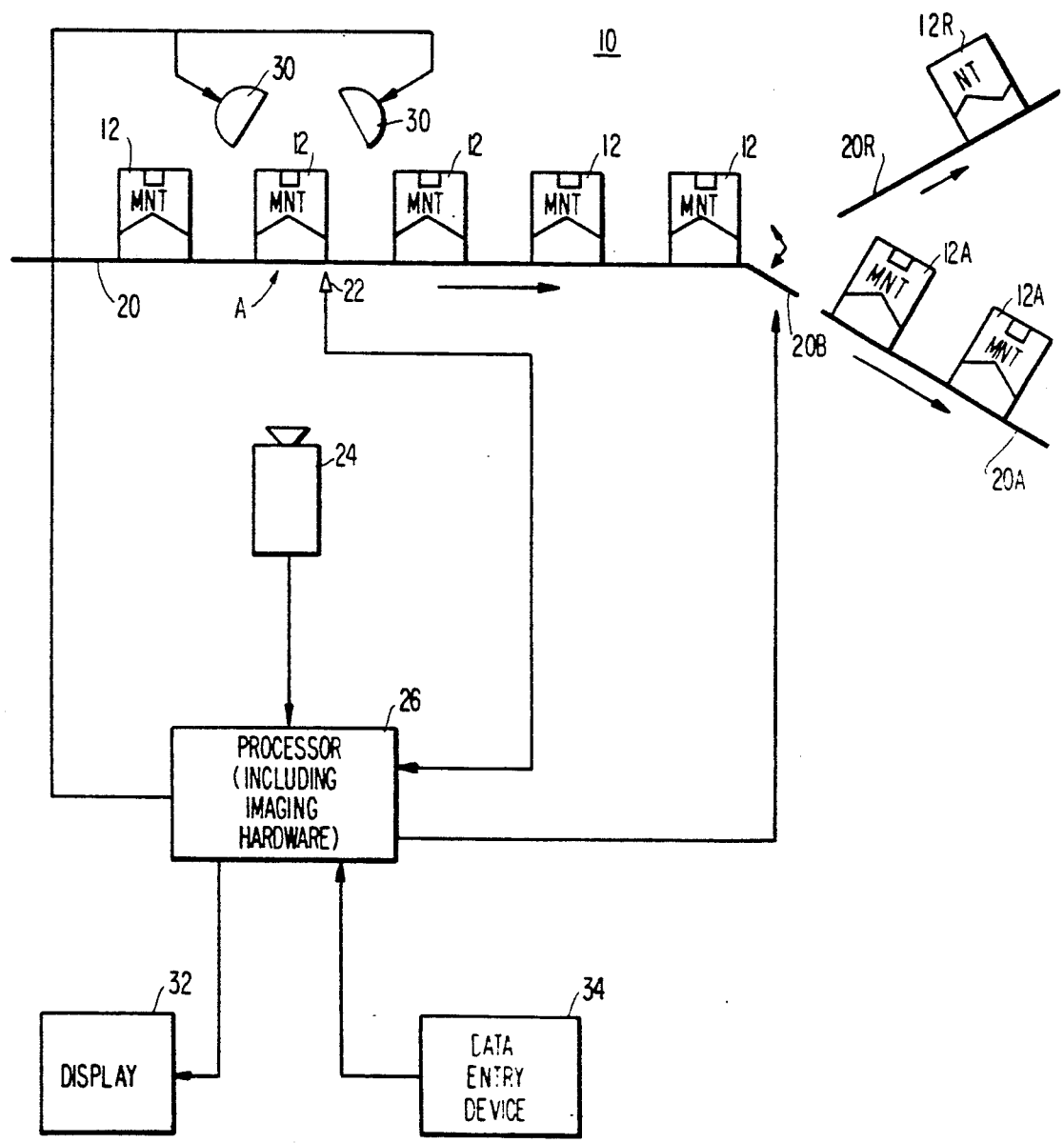
FIG. 1 is a simplified schematic block diagram of an illustrative embodiment of an optical product inspection apparatus constructed in accordance with the principles of this invention.

As shown in FIG. 1, a typical product inspection system 10 constructed in accordance with this invention includes conveyor apparatus 20 for conveying the objects or products 12 to be inspected, one after another, from left to right as viewed in the FIG. Each time conventional product sensor 22 detects a product 12 at a predetermined location A opposite conventional camera 24, conventional processor 26 (which includes conventional imaging hardware) causes conventional light sources 30 to briefly illuminate the product, thereby allowing camera 24 to capture what is effectively a still image of the product. This still image is fed to processor 26 which digitizes and further processes the image. Processor 26 is augmented by conventional video display 32 and conventional data entry device 34 (e.g., a keyboard, mouse, and/or touch screen elements associated with display 32). Processor 26 can cause display 32 to display a product image captured by camera 24, and can augment that display with other information such as the outline of an acceptable product image and/or outlines of certain features of an acceptable product image. The operator may use this augmenting information to help determine whether the product image being displayed is acceptable. The operator may use data entry device 34 to control the overall operation of the system, as well as to respond to inquiries from the system (e.g., as to whether or not the operator judges the product image currently shown on display 32 to be acceptable).

The system may be set up to perform a product inspection by operating it substantially as though it were inspecting products, i.e., by using conveyor 20 to convey representative products one after another past camera 24 and by using the other elements of the system to process the images of those products as described in detail below. During actual product inspection, processor 26 determines whether the image of each successive product 12 is acceptable, and when that product reaches a controllable branch 20B in conveyor 20, processor 26 controls that branch so that acceptable products 12A are directed to accepted product conveyor 20A, while unacceptable products 12R are directed to rejected product conveyor 20R.

While FIG. 1 suggests that system 10 operates on a single elevational image of products 12, it will be apparent to those skilled in the art that the system could be set up to test multiple images of the products taken from different angles and including perspective views so that as many surfaces of the objects are inspected as are desired. Similarly, although the system will be explained in terms of monochrome (e.g., black and white) images, it will be apparent to those skilled in the art how the system can be modified to inspect in full color. Thus camera 24 may be a conventional NTSC or RGB compatible camera. Processor 26 may be a suitably programmed conventional 386 personal computer workstation such as a CAT386 workstation available from Comark Corp. of Medfield, Mass. with a conventional IM-1280 imaging hardware system available from MATROX Electronic Systems Limited of Dorval, Quebec, Canada.

Figure 2A:
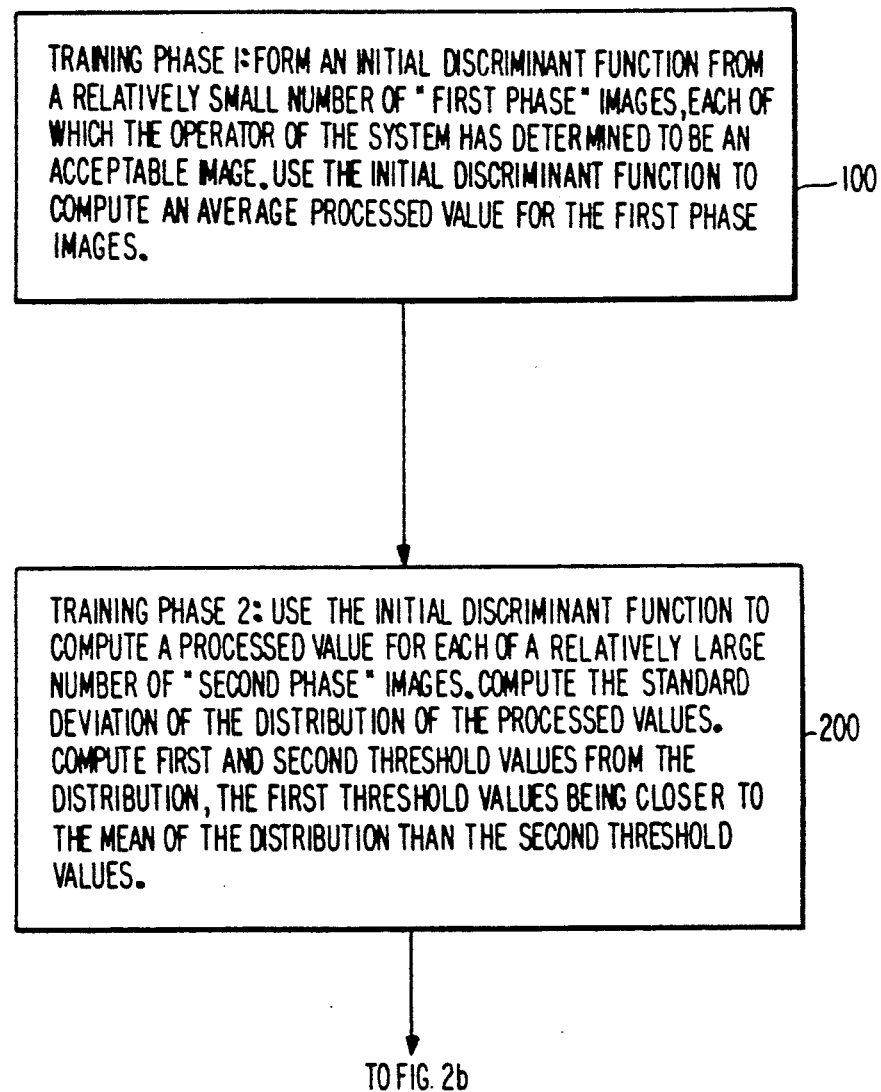

An overview of a preferred embodiment of the method of this invention is shown in FIG. 2. Basically the depicted embodiment comprises a training portion, including three successive phases 1, 2, and 3 (shown in boxes 100, 200, and 300, respectively), and actual product inspection (shown in box 400). During the three training phases, the system "learns", by appropriately processing product images with appropriate but relatively limited input from the human operator of the system, how to discriminate between good and bad images. Thereafter, during actual product inspection, the system uses this "knowledge" to accept or reject products.

Figure 3A:
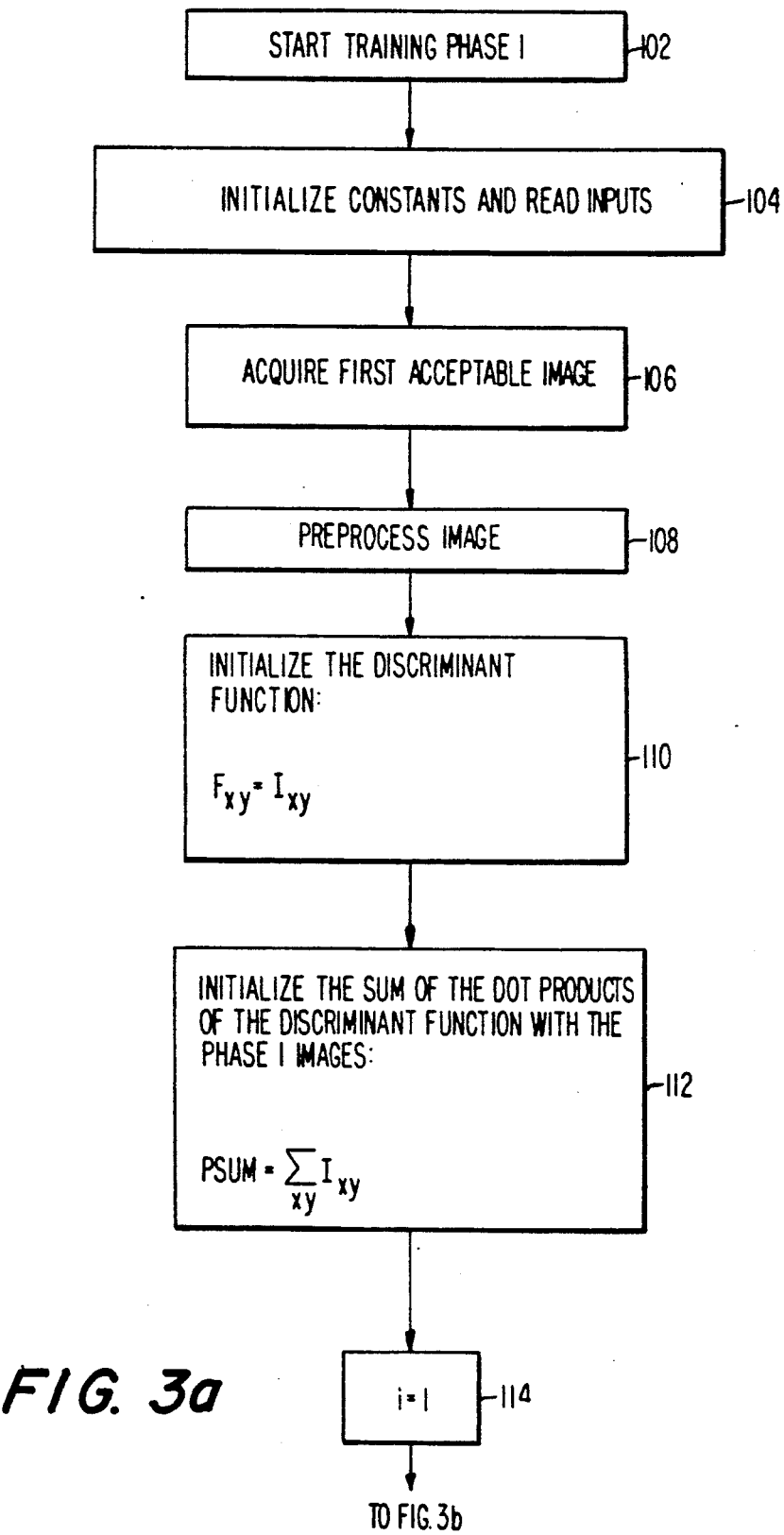
FIGS. 3a-3c (referred to collectively as FIG. 3) are a flow chart of an illustrative, more detailed embodiment of one of the steps shown in FIG. 2.
Figure 3B:
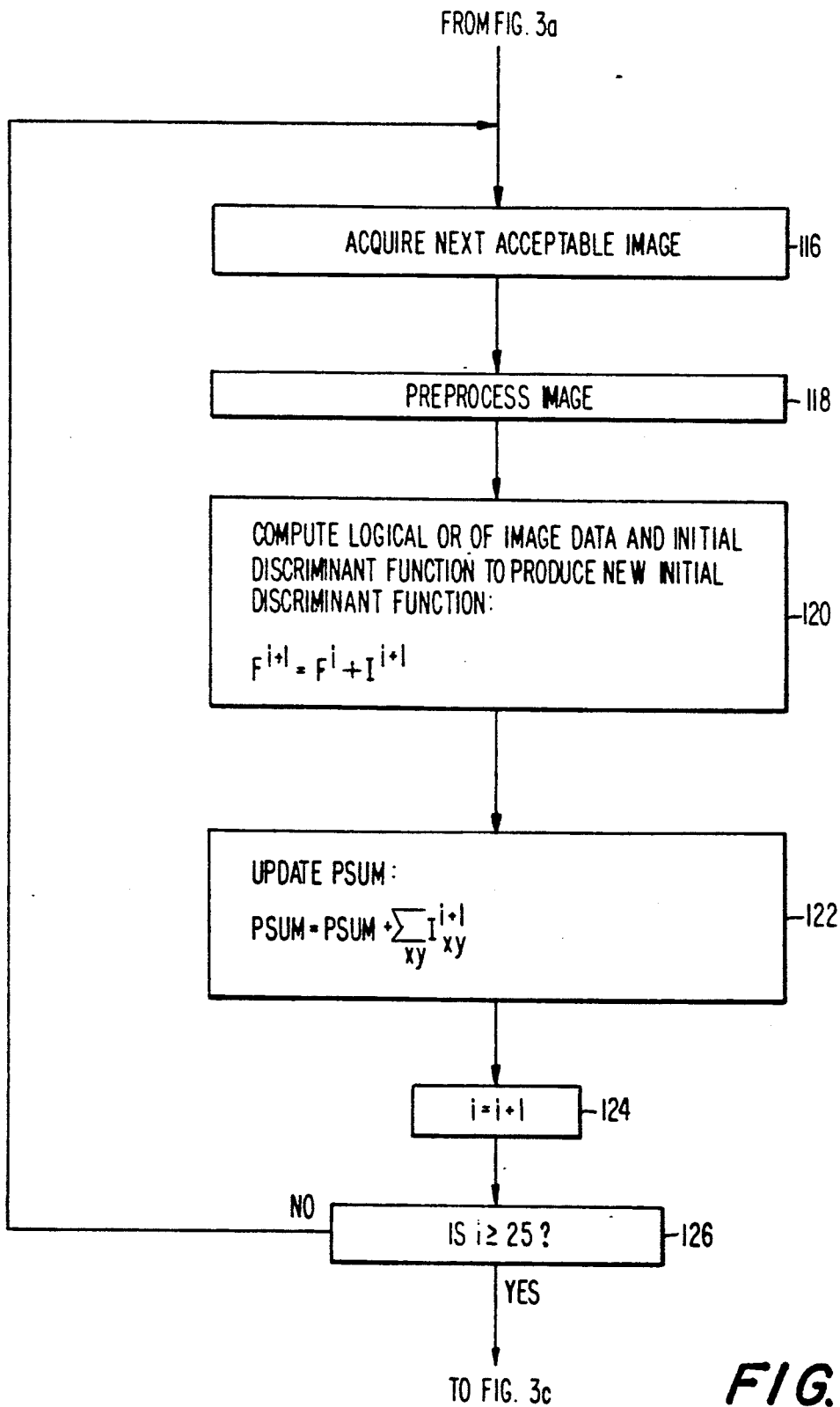
Figure 3C:
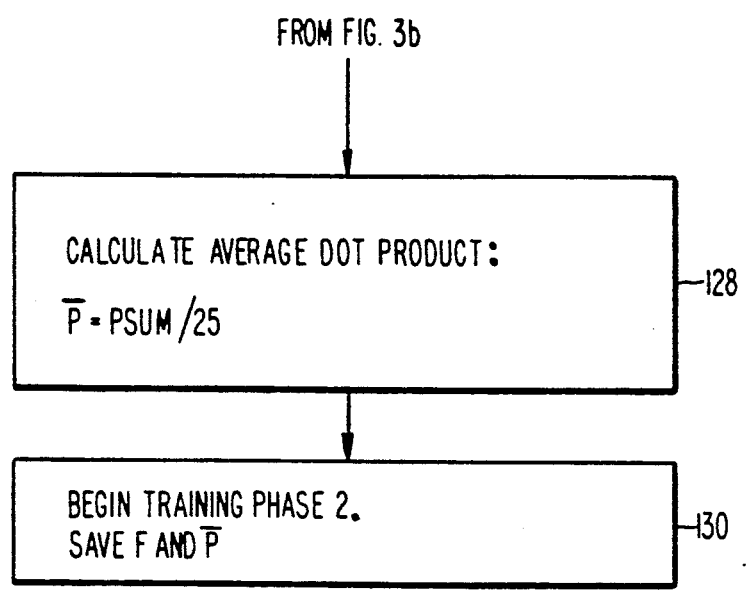

In training phase 1 (step 100 in FIG. 2) an initial discriminant function F (which may be thought of as a two-dimensional matrix commensurate with the two-dimensional data for the product images or product image portions to be inspected) is formed from the data I for a relatively small number of "first phase" images. Although this initial discriminant function could be computed in many other ways in accordance with this invention, in the preferred embodiment (shown in detail in FIG. 3) a relatively simple technique (i.e., a logical OR of the phase 1 images) is used in order to allow a relatively small and inexpensive processor 26 to perform the necessary calculations without requiring more time than the operator of the system needs to provide the necessary inputs regarding each successive first phase image. Accordingly, as shown in FIG. 3 training phase 1 starts with step 102, and in step 104 various program constants are initialized and inputs are read (e.g., from the memory which is part of processor 26 and/or from data entry device 34). For example, step 104 may include selection of an image outline overlay to be displayed with product images on display 32 to help the operator judge the acceptability of images. Step 104 may also include selection of the boundaries of the portion or portions of the image to be processed. As another example, step 104 may include selection of a threshold to be used in binarizing the image data as discussed below. Any other necessary system initialization tasks may be performed as part of step 104.

In step 106 the system acquires the data for the first of the first phase images. This is done by having camera 24 capture a product image as described above. Processor 26 then digitizes this image in full gray scale and causes display 32 to display this gray scale image with any augmenting information (such as an outline overlay) selected in step 104. The operator then indicates (via data entry device 34) whether or not the displayed image is acceptable. If so, control passes to step 108. If not, step 106 is repeated with new product images until an image acceptable to the operator is found.

In step 108 the first acceptable image is preprocessed. This preferably includes edge detecting the gray scale image so that pixels at or near significant changes in image brightness are emphasized (e.g., increased in value) relative to other pixels which are de-emphasized (e.g., decreased in value). Edge detection is a well-known technique which is discussed in more detail, for example, in U.S. patent application Ser. No. 308,739, filed Feb. 9, 1989 and hereby incorporated by reference herein. After edge detection, the edge detected image is preferably binarized so that all pixels having values on one side of a predetermined binarization threshold level (which may have been selected in step 104) are assigned one binary value (e.g., 1), while all pixels having values on the other side of the binarization threshold level are assigned the other binary value (e.g., 0).

In step 110 the initial discriminant function F is set equal to the first acceptable image data from step 108.

In step 112 the sum of the dot products of the discriminant function and the phase 1 image data is initialized. Because at this point F and I are the same, the initial dot product of F and I is just the sum of the pixel values of I.

In step 114 an index value i is set equal to 1.

In step 116 the system acquires the next acceptable image. Step 116 is therefore an exact repetition of above-described step 106.

In step 118 the data for the next acceptable image (acquired in step 116) is preprocessed exactly as described above in connection with step 108.

In step 12 the initial discriminant function is updated with the new image data by computing the logical OR of the new image data and the old initial discriminant function data to produce a new initial discriminant function. In other words, for each pixel location in which either or both of the image data and the old initial discriminant function data are 1, the new initial discriminant data value is 1, while for each pixel location in which both the image data and the old initial discriminant data are 0, the new initial discriminant function data value is 0.

In step 122 the sum of the dot products of the discriminant function and the phase 1 image data is updated for the current image. Because the 1-valued pixel locations in each image are always a subset of the 1-valued pixel locations in F, each new dot product is just the sum of the pixel values in the current image I.

In step 124 the index i is incremented by 1, and in step 126 the new value of i is tested to determine whether it is greater than or equal to 25. This is an arbitrary number which determines how many first phase images will be used to compute the initial discriminant function. Although any other number could be used, 25 has been found to give good results. If i has not yet reached 25, control returns to step 116 and steps 116–126 are repeated until the test in step 126 is satisfied and control consequently passes to step 128.

In step 128 the average of the dot products of F and each of the first phase images is computed by dividing PSUM by 25 (the number of first phase images).

In step 130 training phase 2 (step 200 in FIG. 2) begins. The initial discriminant function F from the last performance of step 120 and the average dot product are saved.

Figure 4A:
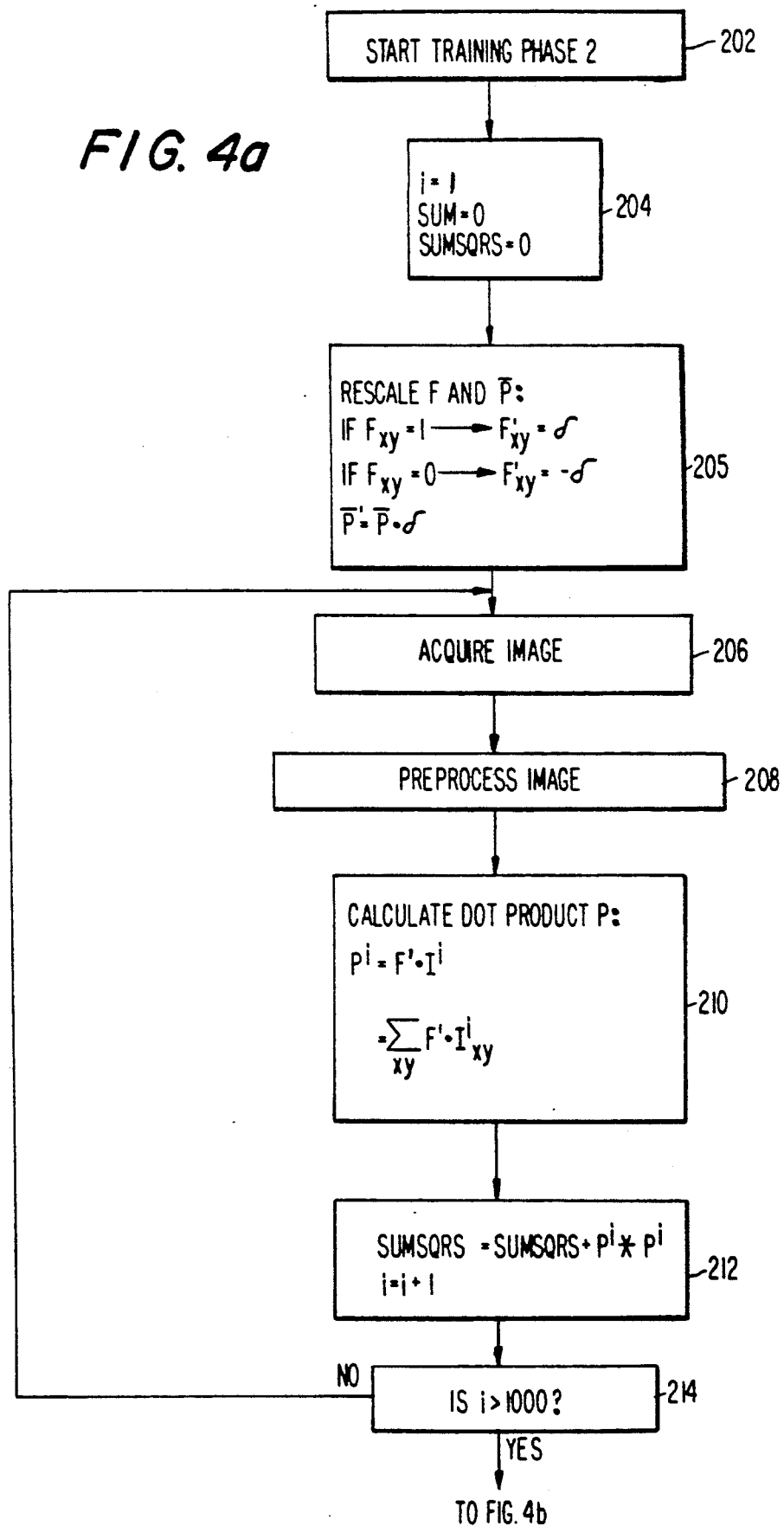
FIGS. 4a and 4b (referred to collectively as FIG. 4) are a flow chart of an illustrative, more detailed embodiment of another one of the steps shown in FIG. 2.
Figure 4B:
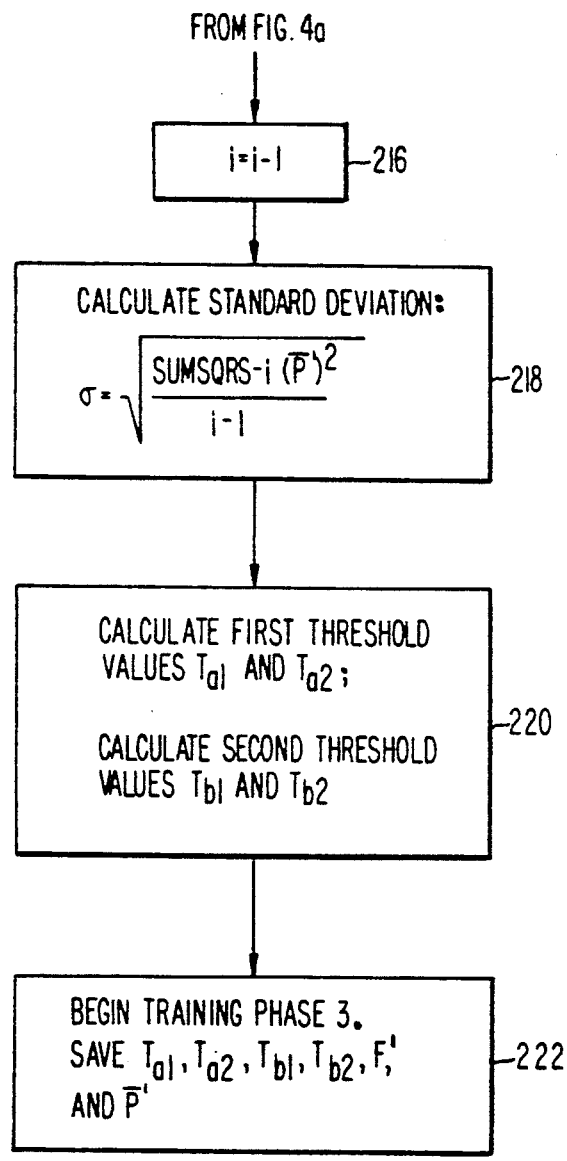

In step 200 the initial discriminant function F is used to compute statistical information about the images being processed. Again, although this can be done in other ways in accordance with this invention, a preferred embodiment of step 200 is shown in FIG. 4 and will now be described by way of illustration.

Training phase 2 starts in step 202. In step 204 index value i is set equal to 1, variable SUM is set equal to 0, and variable SUMSQRS (for sum of squares) is also set equal to 0.

In step 205 the initial binary discriminant function F is converted to bipolar form using initial positive and negative values such that the final discriminant function values take advantage of the full arithmetic range of processor 26. To reflect this in the average dot product, the average dot product is also scaled by the same scale factor in step 205. For example, if processor 26 performs 8-bit arithmetic with values between $-128$ and $+127$, the initial values now used in function F may be $-50$ (for pixel locations where the F value was formerly 0) and $+50$ (for pixel values where the F value was formerly 1), and the average dot product from step 128 may be multiplied by 50.

In step 206 a product image is acquired in a manner similar to above-described step 106, except that during training phase 2 the operator of the system is not required to determine whether the image is acceptable. Accordingly, all the images received during phase 2 are used. These images can therefore be expected to exhibit the normal range of variation for the product images that the system will subsequently encounter during actual product inspection. In addition, because no interaction with the operator of the system is required during this phase, the phase 2 images can be processed much faster (e.g., at actual product inspection rates) than the phase 1 images.

In step 208 the image data acquired in step 206 is preprocessed exactly as described above in connection with step 108.

In step 210 the dot product P of the rescaled initial discriminant function F from step 205 and the image data I from step 208 is calculated. This calculation involves multiplying the value of F at each pixel location by the value of I at that pixel location, and then summing all of the resulting products to produce the dot product P. Elsewhere in this specification the more generic term "processed value" is sometimes used for the dot product P. It will be noted that if I is identical to F, P will be a certain number, but if I differs from F at certain pixel locations, P will be greater or less than that number. The amount by which P differs from that number is a measure of how much I differs from F. In practice, the values of P will typically exhibit an approximately normal (i.e., approximately Gaussian) distribution about some mean or average value.

In step 212 the variable SUMSQRS is incremented by the square of the value of P from step 210, and the index value i is incremented by 1.

In step 214 the index value i is compared to an arbitrary number (e.g., 1000) which is the predetermined number of images to be processed in phase 2. Although any sufficiently large number of images can be processed in phase 2, 1000 images have been found to give good results. If the test in step 214 is not satisfied, control returns to step 206 where processing of the next phase 2 image begins. When 1000 phase 2 images have been processed as described above, the test in step 214 is satisfied and control passes from step 214 to step 216.

In step 216 the index value i is reduced by 1 to reverse the last incrementing of that value.

In step 218 the rescaled average dot product from step 205 and the value of the SUMSQRS variable are used to compute the standard deviation of the previously computed dot products.

In step 220 two first threshold values and two second threshold values are selected so that the distribution of phase 2 dot products is subdivided by these threshold values as shown in FIG. 7. For example, the first threshold values may be chosen so that a fraction f1 of the dot products are greater than the upper one of these threshold values and the same fraction of dot products are less than the lower one of these threshold values. The fraction f1 is preferably significantly greater than one-half the fraction of images which are expected to be defective in order to minimize the possibility that any unacceptable images have dot products that are greater than the upper or less than the lower of these first threshold values. Images with dot products between the first threshold values are therefore automatically acceptable as indicated in FIG. 7.

The second threshold values are chosen so that a smaller fraction f2 of the dot products are greater than the upper one of these threshold values and the same smaller fraction of dot products are less than the lower one of these threshold values. The fraction f2 is preferably significantly smaller than one-half the fraction of images which are expected to be defective in order to minimize the possibility that any acceptable images have dot products that are less than the lower or greater than the upper one of these second threshold values. Images with dot products outside the region bounded by the second threshold values are therefore automatically rejectable as "gross rejects" as indicated in FIG. 7. Images with dot products outside the region bounded by the first threshold values but inside the region bounded by the second threshold values are "marginal rejects" as indicated in FIG. 7. Operator intervention is required to determine whether such an image should be accepted or rejected.

It may be convenient and appropriate to choose the threshold values described above assuming the distribution of dot products to be Gaussian as shown, for example, in FIG. 8, and therefore characterized by a standard deviation (given by the equation in step 128). In that case, the thresholds can be defined by the equations shown in FIG. 9. The average dot product used in these equations is the rescaled average dot product from step 205. The alpha coefficients used in these equations with the standard deviation are selected so as to achieve the target fractions f1 and f2 for a Gaussian distribution. These values can be readily selected with the aid of available tables of the properties of the Gaussian distribution. The most preferred approach is to select the first threshold values without assuming a Gaussian distribution (i.e., as described prior to the above discussion of the Gaussian distribution), and to use the second method (i.e., the Gaussian distribution assumption) to select the second threshold values. Note that in FIG. 8 the region A corresponds to the "acceptable" region of FIG. 7, the regions B correspond to the "gross reject" regions of FIG. 7, and the regions C correspond to the "marginal reject" regions of FIG. 7. Thus region A includes dot products known to be associated with clearly acceptable images, whereas regions B include dot products known to be associated with clearly unacceptable images. Regions C are those along the distribution of dot products P which may be marginally acceptable. Adaptive training is performed in phase 3 as discussed below with respect to dot products lying in region A, and also with respect to dot products lying in regions C which the operator of the system determines to be acceptable.

After the second threshold values are calculated in step 220, control passes to step 222 to begin training phase 3 (step 300 in FIG. 2). The first and second threshold values from step 220 are saved, as are F and the rescaled average dot product from step 205.

In training phase 3 (step 300 in FIG. 2) the statistical information from phase 2 is used with the image data from another statistically significant number of images to refine the initial discriminant function F. Again, although this can be done in other ways in accordance with this invention, a preferred embodiment of training phase 3 is shown in FIG. 5 which will now be described by way of illustration.

Figure 5A:
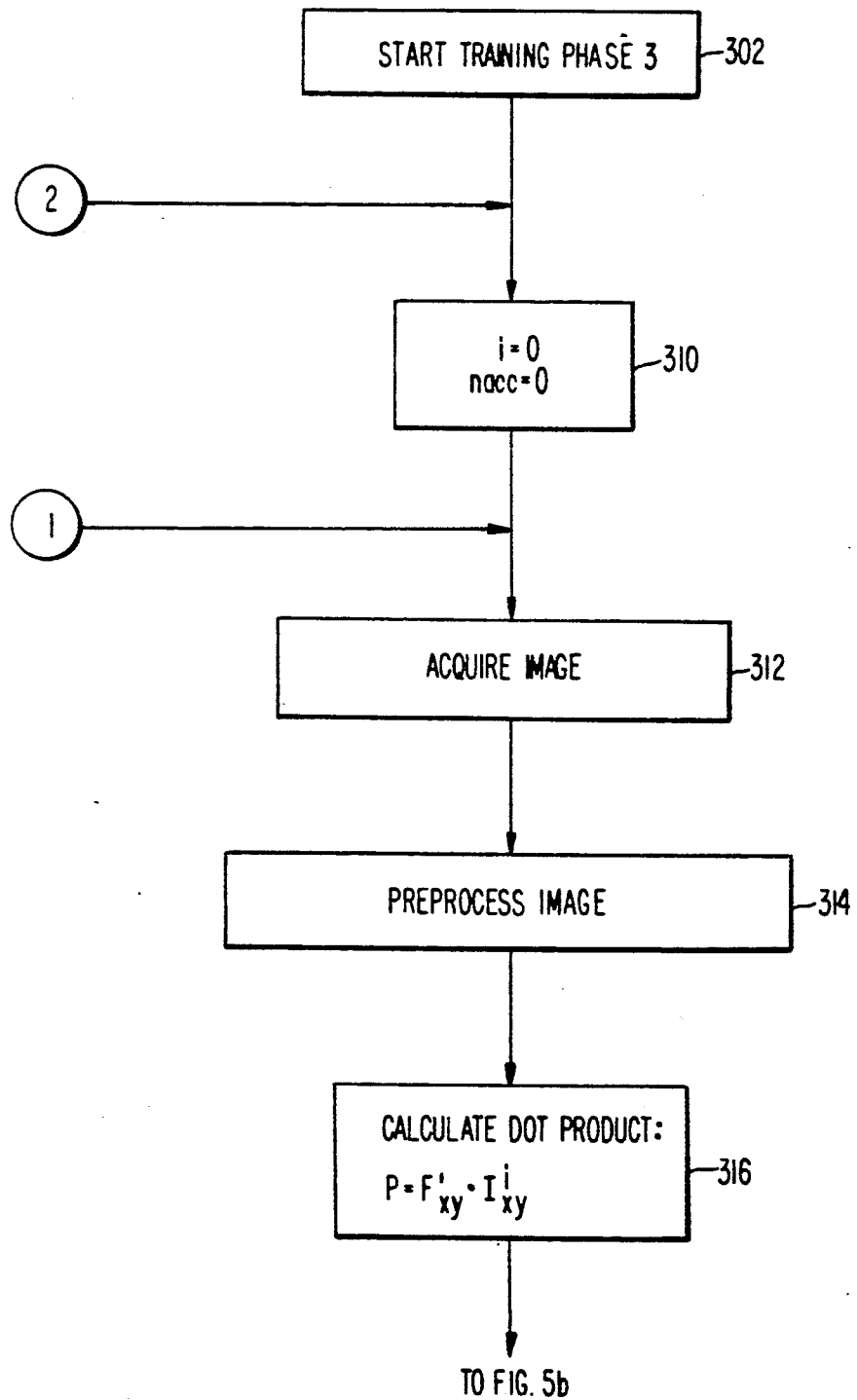
FIGS. 5a-5c (referred to collectively as FIG. 5) are a flow chart of an illustrative, more detailed embodiment of still another one of the steps shown in FIG. 2.
Figure 5B:
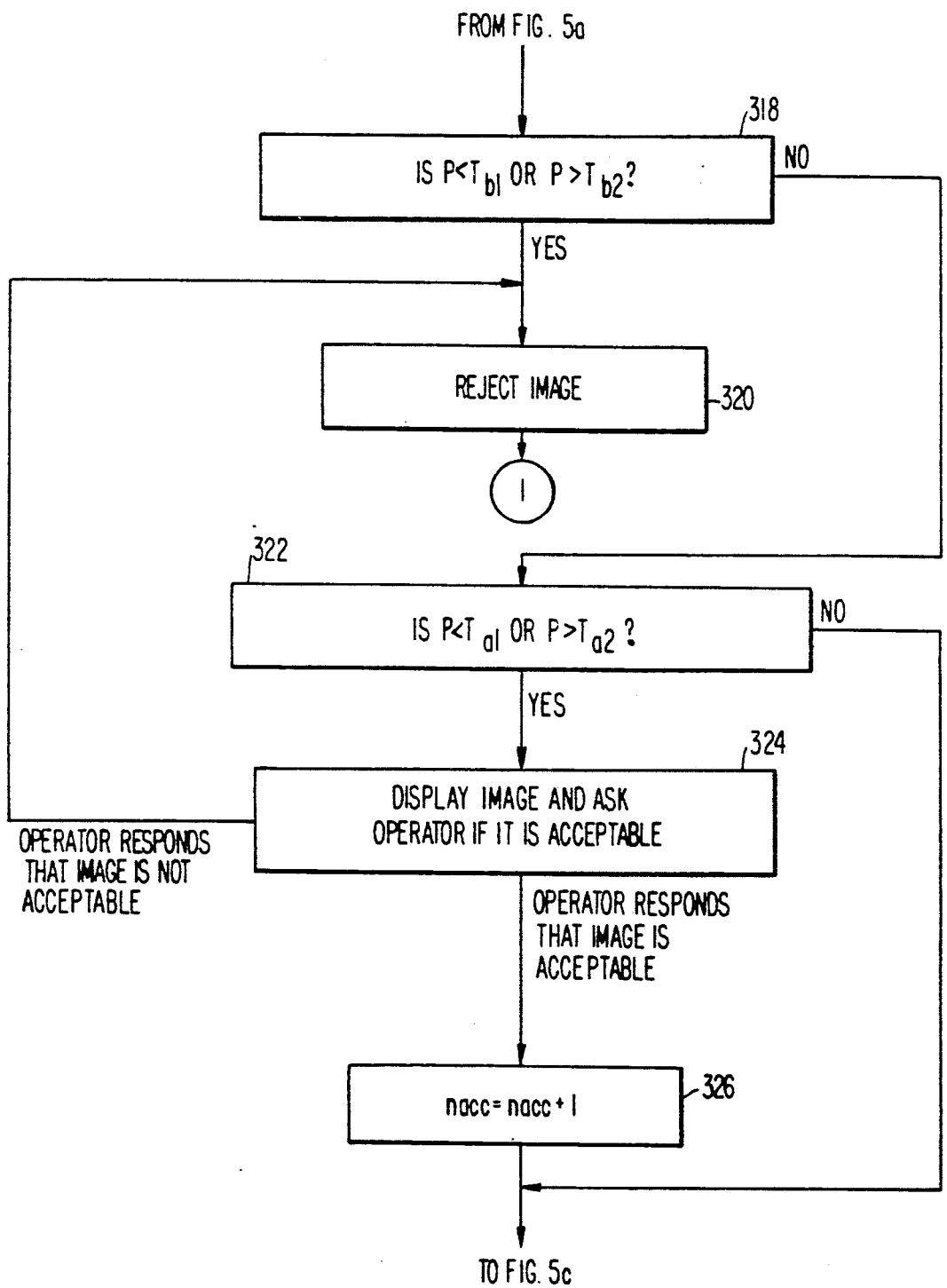
Figure 5C:
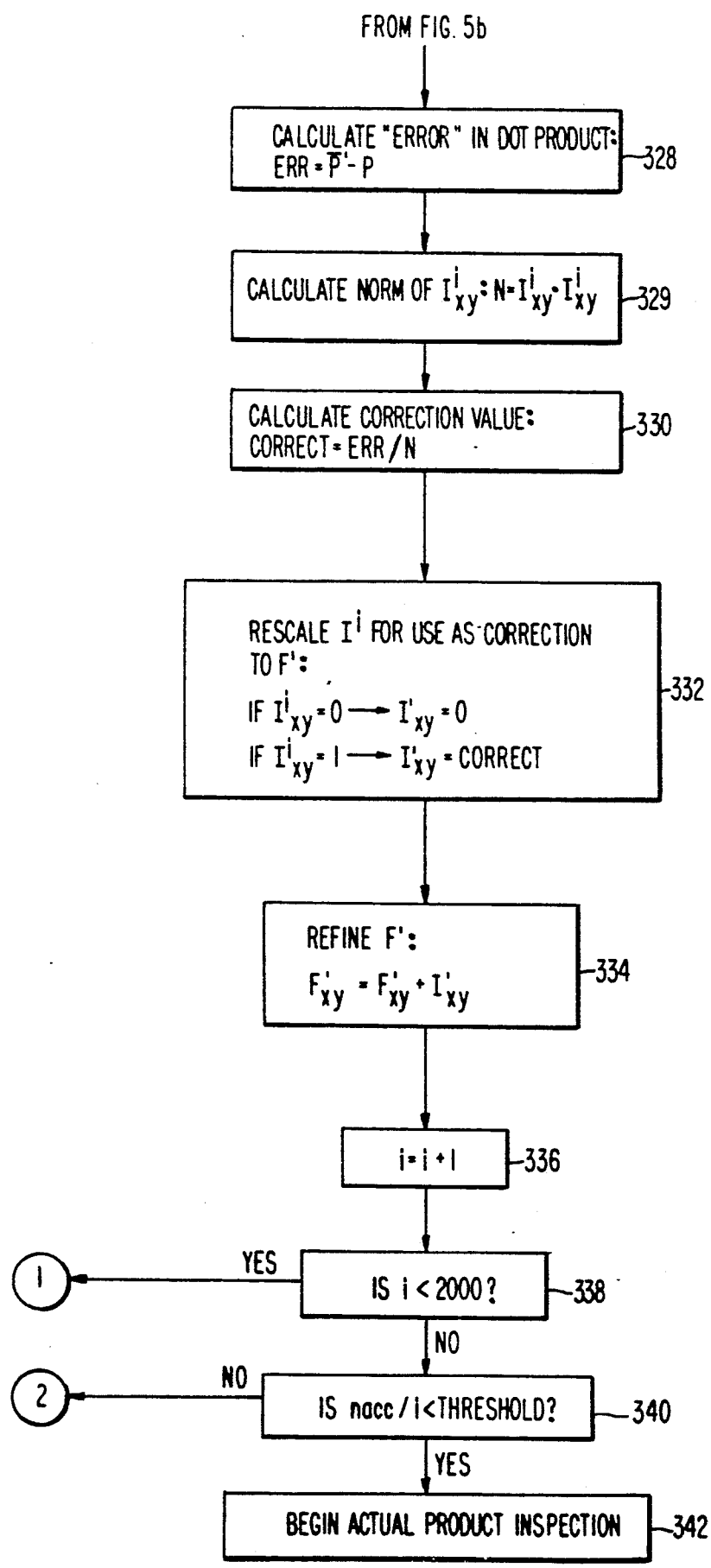

As shown in FIG. 5, training phase 3 begins in step 302, and in step 310 an index value i is initialized to 0, and a counter—used during phase 3 to count the number of marginally acceptable images which the operator of the system decides to accept—is also initialized to 0.

In step 312 a phase 3 image is acquired exactly as described above in connection with step 206, and in step 314 the data for this image is preprocessed as described above in connection with step 208.

In step 316 the dot product P of the discriminant function and the image data from step 314 is calculated.

In step 318 the dot product value P from step 316 is compared to the second threshold values from step 220. If P is outside the range bounded by these second threshold values, control passes to step 320 where the image is rejected and control is then returned to step 312 to begin the acquisition and processing of the next phase 3 image. On the other hand, if P is in the range bounded by the second threshold values, control passes from step 318 to step 322.

In step 322 the value of P from step 316 is compared to the first threshold values from step 220. If P is outside the range bounded by these first threshold values, control passes to step 324. Step 324 is reached whenever the image is neither automatically rejectable as unacceptable (because the associated dot product is outside the limits defined by the second threshold values), nor automatically acceptable (because the associated dot product is inside the limits defined by the first threshold values). Accordingly, in step 324 the operator of the system is asked to intervene and decide whether or not the image is acceptable. The image is displayed on display 32 (as in connection with step 106 above). If the operator responds (again as in connection with step 106) that the image is unacceptable, control passes to step 320 where the image is rejected, and thereafter processing of the next phase 3 image begins as described above. On the other hand, if the operator responds that the image is acceptable, control passes from step 324 to step 326 where the counter nacc is incremented. Thereafter, control passes to step 328. Returning to the other branch from step 322, if P is not outside the limits defined by the first threshold values, the image is automatically acceptable and control passes directly from step 322 to step 328.

Step 328 is performed only when the current third phase image has been determined to be an acceptable image. In most cases the system will have made this determination automatically because the dot product P for the image is between the first threshold values and the image is therefore obviously acceptable. In a few cases, however, the operator will have been required to assist with this determination as described above in connection with step 324. Accordingly, for the most part the processing of images can proceed as rapidly during phase 3 as during phase 2. Only rarely will the operator be required to intervene as a result of the performance of step 324. Moreover, operator intervention should be required even less frequently as phase 3 proceeds and the discriminant function is progressively refined as will now be described.

Step 328 begins the process of refining the rescaled discriminant function using the data from the image which has just been determined to be acceptable. This discriminant function refining process is repeated for each acceptable phase 3 image. In step 328 an "error" value equal to the difference between the average P value from step 205 and P from step 316 is calculated. In step 329 a value N equal to the number of pixels which are "on" in the image data is calculated. In step 330 a correction value equal to the error value from step 328 divided by the value of N from step 329 is calculated. In step 332 the binary image data for the current phase 3 image is rescaled using the correction value from step 330. In particular, each pixel value of 1 is changed to the correction value, while each pixel value of 0 is unaltered.

In step 334 the rescaled discriminant function is refined by incrementing each pixel value by the value associated with that pixel in the rescaled image data from step 332. Step 334 is an "adaptive training" step analogous to the Widrow-Hoff training algorithm sometimes used in signal processing (see, for example, B. Widrow and S. D. Stearns, *Adaptive Signal Processing,* Prentice-Hall, Englewood Clifs, 1985). Accordingly, as step 334 is performed for successive acceptable third phase images, the rescaled discriminant function becomes better and better at producing dot products (as in step 316) which are clearly differentiated between those associated with acceptable images (P within the range bounded by the first threshold values) and those associated with unacceptable images (P outside the range bounded by the second threshold values). Accordingly, as phase 3 progresses, there should be less and less need to perform step 324, and the amount of input required from the operator of the system should decrease.

In step 336 the index value i is incremented. In step 338 this index value is compared to a phase 3 cut-off value (e.g., 2000 acceptable phase 3 images). If the index value is less than the cut-off value, control passes from step 338 to step 312 where processing of the next phase 3 image begins. As soon as step 338 detects that the index value has reached the cut-off value, control passes from step 338 to step 340.

In step 340 the ratio of the counter value nacc to the index value i is compared to a predetermined threshold value. If this ratio exceeds the threshold value, the system is still tentatively rejecting too many images which the operator of the system has found acceptable in step 324. This indicates that the discriminant function F' is still in need of further refinement. Accordingly, control passes from step 340 to step 310 where the processing of another series of phase 3 images begins again. On the other hand, if the ratio in step 340 is less than the threshold, the refining of discriminant function F' is judged complete, and training phase 3 is concluded by passing control to step 342 where actual product inspection begins (step 400 in FIG. 2).

Figure 6:
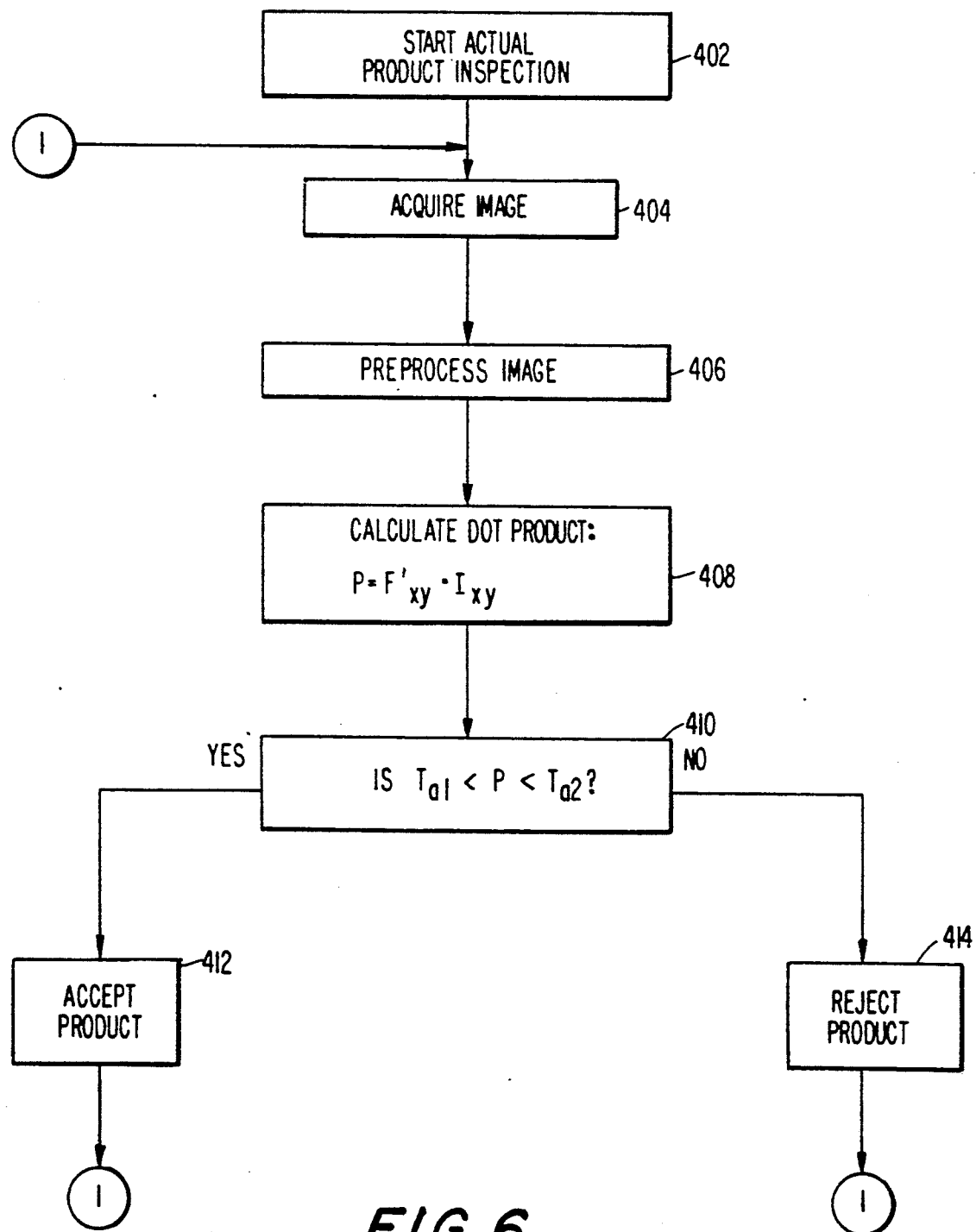
FIG. 6 is a flow chart of an illustrative, more detailed embodiment of yet another one of the steps shown in FIG. 2.

An illustrative embodiment of actual product inspection (step 400 in FIG. 2) is shown in FIG. 6. This process begins with step 402, and in step 404 an image is acquired as in step 206. In step 406 the data for this image is preprocessed as in step 208. In step 408 the dot product P of the refined discriminant function from training phase 3 and the image data from step 406 is calculated. In step 410 P is tested to determine whether or not it is in the range between the first threshold values from step 220. If so, the system deems the image acceptable and control passes to step 412 in order to accept the product (i.e., direct it to accepted product conveyor 20A in FIG. 1). If the step 410 test is not satisfied, the system deems the image unacceptable and control passes to step 414 in order to reject the product (i.e., direct it to rejected product conveyor 20R in FIG. 1). After either step 412 or 414, control returns to step 404 to begin processing of the next image.

It will be understood that the foregoing is merely illustrative of the principles of this invention and that various modifications can be made by those skilled in the art without departing from the scope and spirit of the invention. For example, each image formed by elements 24 and 26 can be broken down into a plurality of predetermined segments, and the data for each of the segments can be separately processed just as the data for the whole image is processed in the foregoing discussion. During actual product inspection all segments must satisfy the test of step 410 in order for the product to be accepted. As another example of a modification within the scope of this invention, discriminant function F' can continue to be refined during actual product inspection by updating it in accordance with any acceptable product image or images exactly as described above in connection with training phase 3.

The invention claimed is:

1. The method of determining the acceptability of the appearance of each of a plurality of objects comprising the steps of:

forming an image of each of a first subplurality of said objects;

combining the images of said first subplurality to produce an initial discriminant function;

forming an image of each of a second subplurality of said objects;

using said initial discriminant function to process each of the images of said second subplurality in order to produce a processed value for each of said images from said second subplurality which is indicative of how similar said image from said second subplurality is to said initial discriminant function;

selecting first processed value thresholds between which a first majority of said processed values fall;

selecting second processed value thresholds between which a second majority of said processes values fall, said second majority being larger than said first majority;

forming an image of each of a third subplurality of said objects;

using selected images of said third subplurality to progressively refine said discriminant function by (1) using said discriminant function to process each successive image from said third subplurality in order to produce a processed value for said image from said third subplurality, (2) determining whether said processed value is substantially between said second value thresholds, and (a) if not, discarding said image from said third subplurality and skipping step (3) below, or (b) if so, determining whether said processed value is substantially between first processed value thresholds, and (i) if so, continuing with step (3) below, or (ii) if not, discarding said image from said third subplurality and skipping step (3) below unless said image from said third subplurality appears acceptable, and (3) modifying said discriminant function in accordance with said image from said third subplurality;

forming an image of each of a fourth subplurality of said objects; and using the refined discriminant function to determine whether or not each of the images of said fourth subplurality has an acceptable appearance.

2. The method defined in claim 1 wherein adaptive training is used in said step of modifying said discriminant function in accordance with said image from said third subplurality.

3. The method defined in claim 1 further comprising the step of:

separating the objects in said fourth subplurality whose images have been determined to have an acceptable appearance from the objects in said fourth subplurality whose images have been determined to not have an acceptable appearance.

4. The method defined in claim 1 wherein said step of using said refined discriminant function comprises the steps of:

using the refined discriminant function to process each of the images of said fourth subplurality in order to produce a processed value for said image from said fourth subplurality; and comparing said processed value to said first processed value thresholds and identifying said image from said fourth subplurality as having an acceptable appearance only if said processed value is substantially between first processed value thresholds.

5. The method defined in claim 1 wherein at least one of said steps of forming an image comprises the steps of:

subdividing the image being formed in said at least one of said steps of forming an image into a plurality of pixels, each of which has an initial digital value indicative of the appearance of the associated portion of the associated object;

processing said initial digital values to produce edge detected digital values which emphasize edges in said image being formed; and converting each edge detected digital value which is greater than a predetermined value to one of first and second numerical values, and converting each edge detected digital value which is not greater than said predetermined value to the other of said first and second numerical values.

6. The method defined in claim 5 wherein said step of forming an image of each of said first subplurality of objects is performed using the steps set forth in claim 5, and wherein said step of combining the images of said first subplurality of objects comprises the step of:

producing said initial discriminant function as the logical OR of all of said images of said first subplurality of said objects.

7. The method defined in claim 1 wherein said step of using said initial discriminant function comprises the step of:

calculating the dot product of said initial discriminant function and each of the images of said second subplurality of objects.

8. The method defined in claim 1 wherein said first majority of said processed values is a subset of said second majority of said processed values.

9. The method defined in claim 1 wherein substep (1) comprises the step of:

calculating the dot product of said discriminant function and each successive image of an object from said third subplurality.

10. The method of processing a plurality of images to produce an image discriminant function comprising the steps of:

subdividing a first of said images into a plurality of pixels, each of which has an initial digital value proportional to a predetermined image characteristic of the associated portion of the associated image;

assigning a first numerical value to each pixel having an initial digital value which is on one side of a predetermined threshold value and assigning a second numerical value to each pixel having an initial digital value which is on the other side of said threshold value to produce an initial discriminant function;

subdividing each remaining image in said plurality of images into a plurality of pixels, each of which has an initial digital value proportional to said predetermined image characteristic of the associated portion of the associated image;

assigning said first numerical value to each pixel in each remaining image having an initial digital value which is on one side of said threshold value and assigning said second numerical value to each pixel in each remaining image having an initial digital value which is on the other side of said threshold value; and producing said image discriminant function by sequentially performing the logical OR operation between each of said remaining images after assigning said numerical values and the initial discriminant function, the result of each logical OR operation replacing said initial discriminant function for the next performance of said logical OR operation.

11. The method defined in claim 10 wherein said subdividing step comprises the step of:

edge detecting each of said images so that said initial digital values emphasize edges in said image.

12. The method defined in claim 1 wherein at least one of said steps of forming an image of an object comprises the step of positioning said object in the field of view of a video camera.

13. The method defined in claim 12 wherein said positioning step comprises the steps of:

conveying said objects one after another through the field of view of said video camera;

detecting when an object is at a predetermined location in said field of view of said video camera; and utilizing the output signal of said video camera concurrent with detection that an object is at said predetermined location as said image of said object.

14. Apparatus for determining the acceptability of the appearance of each of a plurality of objects comprising:

means for forming an image of each of a first subplurality of said objects;

means for combining the images of said first subplurality to produce an initial discriminant function;

means for forming an image of each of a second subplurality of said objects;

means for using said initial discriminant function to process each of the images of said second subplurality in order to produce a processed value for each of said images from said second subplurality which is indicative of how similar said image from said second subplurality is to said initial discriminant function;

means for selecting first processed value thresholds between which a first majority of said processed values fall;

means for selecting second processed value thresholds between which a second majority of said processed values fall, said second majority being larger than said first majority;

means for forming an image of each of a third subplurality of objects;

means for using selected images of said third subplurality to progressively refine said discriminant function by (1) using the discriminant function to process each successive image from said third subplurality in order to produce a processed value for said image from said third subplurality, (2) determining whether said processed value is substantially between said second processed value thresholds, and (a) if not, discarding said image from said third subplurality and skipping (3) below, or (b) if so, determining whether said processed value is substantially between said first processed value thresholds, and (i) if so, continuing with (3) below, or (ii) if not, discarding said image from said third subplurality and skipping (3) below unless said image from said third subplurality appears acceptable, and (3) modifying said discriminant function in accordance with said image from said third subplurality;

means for forming an image of each of a fourth subplurality of said objects; and means for using the refined discriminant function to determine whether or not each of the images of said fourth subplurality has an acceptable appearance.

15. The apparatus defined in claim 14 wherein said means for using selected images of said third plurality employs adaptive training in modifying said discriminant function in accordance with said image from said third subplurality.

16. The apparatus defined in claim 14 further comprising:

means for separating the objects in said fourth subplurality whose images have been determined to have an acceptable appearance from the objects in said fourth subplurality whose images have been determined to not have an acceptable appearance.

17. The apparatus defined in claim 14 wherein said means for using said refined discriminant function comprises:

means for using the refined discriminant function to process each of the images of said fourth subplurality in order to produce a processed value for said image from said fourth subplurality; and means for comparing said processed value to said first processed value thresholds and identifying said image from said fourth subplurality as having an acceptable appearance only if said processed value is substantially between said first processed value thresholds.

18. The apparatus defined in claim 14 wherein at least one of said means for forming an image comprises:

means for subdividing the image being formed by said at least one of said means for forming an image into a plurality of pixels, each of which has an initial digital value indicative of the appearance of the associated object;

means for processing said initial digital values to produce edge detected digital values which emphasize edges in said image being formed; and means for converting each edge detected digital value which is greater than a predetermined value to one of first and second numerical values, and converting each edge detected digital value which is not greater than said predetermined value to the other of said first and second numerical values.

19. The apparatus defined in claim 18 wherein said means for forming an image of each of said first subplurality of objects comprises the means set forth in claim 18, and wherein said means for combining the images of said first subplurality of objects comprises:

means for producing said initial discriminant function as the logical OR of all of said images of said first subplurality of said objects.

20. The apparatus defined in claim 14 wherein said means for using said initial discriminant function comprises:

means for calculating the dot product of said initial discriminant function and each of the images of said second subplurality of objects.

21. The apparatus defined in claim 14 wherein said first majority of said processed values is a subset of said second majority of said processed values.

22. The apparatus defined in claim 14 wherein said means for using selected images of said third subplurality employs means for calculating the dot product of said discriminant function and each successive image from said third subplurality in order to produce said processed value for said image from said third subplurality.

23. The apparatus defined in claim 14 wherein at least one of said means for forming an image comprises:

a video camera; and means for positioning an object in the field of view of said video camera.

24. The apparatus defined in claim 23 further comprising:

means for illuminating said object in the field of view of said video camera.

25. The apparatus defined in claim 23 wherein said means for positioning comprises:

a conveyor for conveying said objects one after another through the field of view of said video camera.

26. The apparatus defined in claim 23 wherein said means for positioning comprises:

means for conveying said objects one after another through the field of view of said video camera;

means for detecting when an object being conveyed by said means for conveying is at a predetermined location in said field of view of said video camera; and means responsive to said means for detecting for utilizing the output signal of said video camera concurrent with detection that an object is at said predetermined location as said image of said object.

27. Apparatus for processing a plurality of images to produce an image discriminant function comprising:

means for subdividing a first of said images into a plurality of pixels, each of which has an initial digital value proportional to a predetermined image characteristic of the associated portion of the associated image;

means for assigning a first numerical value to each pixel having an initial digital value which is on one side of a predetermined threshold value and assigning a second numerical value to each pixel having an initial digital value which is on the other side of said threshold value to produce an initial discriminant function;

means for subdividing each remaining image in said plurality of images into a plurality of pixels, each of which has an initial digital value proportional to said image characteristic of the associated portion of the associated image;

means for assigning said first numerical value to each pixel in each remaining image having an initial digital value which is on one side of said threshold value which is on one side of said threshold value and assigning said second numerical value to each pixel in each remaining image having an initial digital value which is on the other side of said threshold value; and means for producing said image discriminant function by sequentially performing the logical OR operation between each of said remaining images after assigning said numerical values and the initial discriminant function, the result of each logical OR operation replacing said initial discriminant function for the next performance of said logical OR operation.

28. The apparatus defined in claim 27 wherein said means for subdividing comprises:

means for edge detecting each of said images so that said initial digital values emphasize edges in said image.

29. A method of determining the acceptability of a product, comprising the steps of:

generating a filter from a first set of acceptable images of said product;

comparing said filter with a member of a second set of images of said product to produce a processed value, said second set including at least some acceptable images;

repeating said comparing step to produce a distribution of processed values;

generating from said distribution of processed values a first range (A) of processed values, said first range comprising processed values associated with acceptable images of said product;

generating from said distribution of processed values a second range (B) of processed values, said second range comprising processed values associated with unacceptable images of said product;

comparing said filter with a further image of said product so as to produce a further processed value;

generating an indication of acceptability or unacceptability of said further image by comparing said further processed value to said first and second ranges;

if said further processed value is outside both said first and second ranges, selecting said further image only if said further image is acceptable; and adaptively training said filter with said selected further image to produce a modified filter such that comparing said modified filter with said selected further image produces a modified processed value which is within said first range.

30. The method as claimed in claim 29, wherein said step of generating a filter includes combining said first set of acceptable images using a logical OR operation.

31. The method as claimed in claim 29, wherein said adaptively training step is analogous to a Widrow-Hoff training algorithm.

32. The method as claimed in claim 29, wherein said selecting step includes manually selecting according to an appearance of said product associated with said outside processed value.

33. The method as claimed in claim 29, further comprising the step of:

if said further processed value is in said first range, adaptively training said filter with said further image.

34. Apparatus for determining the acceptability of a product, comprising:

means for generating a filter from a first set of acceptable images of said product;

means for comparing said filter with a member of a second set of images of said product to produce a processed value, said second set including at least some acceptable images;

means for repeating said comparing function to produce a distribution of processed values;

means for generating from said distribution of processed values a first range (A) of processed values, said first range comprising processed values associated with acceptable images of said product;

means for generating from said distribution of processed values a second range (B) of processed values, said second range comprising processed values associated with unacceptable images of said product;

means for comparing said filter with a further image of said product so as to produce a further processed value;

means for generating an indication of acceptability or unacceptability of said further image by comparing said further processed value to said first and second ranges;

if said further processed value is outside first and second ranges, means for selecting said further image only if said further image is acceptable; and means for adaptively training said filter with said selected further image to produce a modified filter such that comparing said modified filter with said selected further image produces a modified processed value which is within said first range.

35. The apparatus as claimed in claim 34, wherein said means for generating a filter includes means for combining said first set of acceptable images using a logical OR operation.

36. The apparatus as claimed in claim 34, wherein said means for adaptively training performs a function analogous to a Widrow-Hoff training algorithm.

37. The apparatus as claimed in claim 34, wherein said means for selecting includes means for allowing manual selection according to an appearance of said product associated with said outside processed value.

38. The apparatus as claimed in claim 34, further comprising:

if said further processed value is in said first range, means for adaptively training said filter with said further image.

39. The method of determining whether or not a sample image is substantially similar to a predetermined standard image comprising the steps of:

(a) forming a discriminant function which is representative of said standard image;

(b) comparing each of a first plurality of possible examples of said sample image to said discriminant function to produce a first processed value for each of said first plurality of examples of said sample image, each of said processed values being indicative of how similar the associated example is to said standard image;

(c) comparing a further possible example of said sample image to said discriminant function to produce a further processed value indicative of how similar said further example of said sample image is to said standard image;

(d) using said first processed values to at least partly determine whether said further possible example of said sample image is substantially similar to said standard image, and if so, modifying said discriminant function in accordance with said further example of said sample image;

(e) repeating steps (c) and (d) for each of a plurality of further possible examples of said sample image to progressively modify said discriminant function; and (f) comparing said sample image to the modified discriminant function to produce a sample processed value indicative of how similar said sample image is to said standard image.

40. Apparatus for determining whether or not a sample image is substantially similar to a predetermined standard image comprising:

means for forming a discriminant function which is representative of said standard image;

means for comparing each of a first plurality of possible examples of said sample image to said discriminant function to produce a first processed value for each of said first plurality of examples of said sample image, each of said processed values being indicative of how similar the associated example is to said standard image;

means for comparing a further possible example of said sample image to said discriminant function to produce a further processed value indicative of how similar said further example of said sample image is to said standard image;

means for using said first processed values to at least partly determine whether said further possible example of said sample image is substantially similar to said standard image, and of so, modifying said discriminant function in accordance with said further example of said sample image;

means for repeating the two preceding functions for each of a plurality of further possible examples of said sample image to progressively modify said discriminant function; and means for comparing said sample image to the modified discriminant function to produce a sample processed value indicative of how similar said sample image is to said standard image.

41. The method defined in claim 5 wherein said numerical values are binary 0 and 1.

42. The method defined in claim 10 wherein said numerical values are binary 0 and 1.

43. The apparatus defined in claim 18 wherein said numerical values are binary 0 and 1.

44. The apparatus defined in claim 17 wherein said numerical values are binary 0 and 1.

* * * * *